US006897340B2

(12) United States Patent
Borochovitch et al.

(10) Patent No.: US 6,897,340 B2
(45) Date of Patent: May 24, 2005

(54) PROCESSES FOR PREPARATION OF POLYMORPHIC FORM II OF SERTRALINE HYDROCHLORIDE

(75) Inventors: Ronen Borochovitch, Netanya (IL); Marioara Mendelovici, Rechovot (IL); Tamar Nidam, Yehud (IL); Ruth Tenengauzer, Hod Hasharon (IL); Julia Hrakovsky, Rosh-Ha-Ayin (IL); Judith Aronhime, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/426,468

(22) Filed: Apr. 29, 2003

(65) Prior Publication Data

US 2004/0030190 A1 Feb. 12, 2004

Related U.S. Application Data

(60) Provisional application No. 60/376,787, filed on Apr. 29, 2002.

(51) Int. Cl.$^7$ ............................................. C07C 211/42
(52) U.S. Cl. ....................................... 564/428; 564/424
(58) Field of Search ................................. 564/424, 428

(56) References Cited

U.S. PATENT DOCUMENTS

| | | | |
|---|---|---|---|
| 4,536,518 A | 8/1985 | Welch, Jr. et al. | |
| 5,082,970 A | 1/1992 | Braish | |
| 5,248,699 A | 9/1993 | Sysko et al. | |
| 5,463,126 A | 10/1995 | Williams | |
| 5,734,083 A | 3/1998 | Wilson et al. | |
| 6,452,054 B2 | 9/2002 | Aronhime et al. | |
| 6,495,721 B1 | 12/2002 | Schwartz et al. | |
| 6,500,987 B1 | 12/2002 | Schwartz et al. | |
| 6,552,227 B2 | 4/2003 | Mendelovici et al. | |
| 2004/0132828 A1 | 7/2004 | Van Der Schaaf et al. | |

FOREIGN PATENT DOCUMENTS

| | | |
|---|---|---|
| IN | 765/MAS/00 | 9/2000 |
| JP | 2000-26378 | 1/2000 |
| JP | 2000-26379 | 1/2000 |
| WO | WO 98/27050 | 6/1998 |
| WO | WO 99/47486 | 9/1999 |
| WO | WO 99/57093 | 11/1999 |
| WO | WO 00/32551 | 6/2000 |
| WO | WO 01/16089 | 3/2001 |
| WO | WO 01/30742 | 5/2001 |
| WO | WO 01/32601 | 5/2001 |
| WO | WO 01/45692 | 6/2001 |
| WO | WO 01/90049 | 11/2001 |
| WO | WO 02/096859 | 12/2002 |

OTHER PUBLICATIONS

Declaration of Professor Gautam R. Desiraju, Ph.D., 2004.
The Patents Act, 1970 (39 of 1970), Notice of Opposition to Grant of a Patent (See Section 25; Rule 55).
Written Statement of Opposition to Grant of a Patent (Under Rule 57 of the Patents Rules, 2003 to the Patents Act, 1977).
U.S. Appl. No. 10/198,546, filed Jul. 18, 2002, Schwartz et al.
G.M. Wall, "Pharmaceutical Applications of Drug Crystal Studies," Pharmaceutical Manufacturing, vol. 3, No. 2, Feb. 1986, pp. 33–42.
J. Haleblian et al., "Pharmaceutical Applications of Polymorphism," Journal of Pharmaceutical Sciences, vol. 58, No. 8, Aug. 1969, pp. 911–929.
J.K. Haleblian, "Characterization of Habits and Crystalline Modification of Solids and Their Pharmaceutical Applications," Journal of Pharmaceutical Sciences, vol. 64, No. 8, Aug. 1975, pp. 1269–1288.
Welch et al., "Nontricyclic Antidepressant Agents Derived from cis–and trans–1–Amino–4–aryltetralins," Journal of Medicinal Chemistry, vol. 27, No. 11, Nov. 1984, pp. 1508–1515.

*Primary Examiner*—Brian Davis
(74) *Attorney, Agent, or Firm*—Kenyon & Kenyon

(57) ABSTRACT

Provided are processes for preparation of crystalline sertraline hydrochloride Form II substantilly free of other polymorphic forms of sertraline hydrochloride, preferably on an industrial scale.

39 Claims, 3 Drawing Sheets

X-Ray powder diffraction pattern of pure Sertraline HCl form II

X-Ray powder diffraction pattern of Sertraline HCl form I

X-Ray powder diffraction pattern of Sertraline HCl form II containing form I (2%)

PROCESSES FOR PREPARATION OF POLYMORPHIC FORM II OF SERTRALINE HYDROCHLORIDE

CROSS REFERENCE TO RELATED APPLICATION

This application claims the benefit under 35 U.S.C. §119 (c) of provisional application Ser. No. 60/376,787, filed Apr. 29, 2002 which is incorporated herein by reference.

FIELD OF THE INVENTION

The present invention relates to the solid state chemistry of sertraline hydrochloride.

BACKGROUND OF THE INVENTION

Sertraline hydrochloride, (1S-cis)-4-(3,4 dichlorophenyl)-1,2,3,4-tetrahydro-N-methyl-1-naphthalenamine hydrochloride, having the formula:

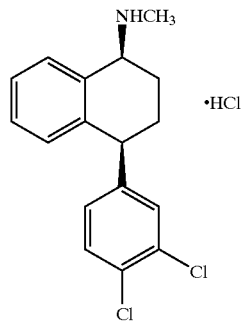

is approved, under the trademark Zoloft®, by the U.S. Food and Drug Administration, as a serotonin re-uptake inhibitor for the treatment of depression, obsessive-compulsive disorder, panic disorder and post-traumatic disorder. In the solid state, sertraline hydrochloride exists in various crystalline forms having different physical properties.

The present invention relates to the solid state physical properties, i.e., polymorphism, of sertraline hydrochloride. These properties may be influenced by controlling the conditions under which sertraline hydrochloride is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account when developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid may have therapeutic consequences because it imposes an upper limit on the rate at which an orally-administered active ingredient may reach the bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC), and may be used to distinguish some polymorphic forms from others. A particular polymorphic form may also give rise to distinct properties that may be detectable by powder X-ray diffraction, solid state $^{13}$C NMR spectrometry and infrared spectrometry.

A solid form (polymorph) of sertraline hydrochloride is disclosed for example in WO 01/90049, which is directed to amorphous form of sertraline hydrochloride. The solid state chemistry of sertraline hydrochloride is also disclosed in JP 0026378 and JP 0026379. According to the English abstract of JP 0026379, "a sertraline free base is dissolved in a solvent (e.g. an ester-based organic solvent such as ethyl acetate, butyl acetate or the like or a ketone-based organic solvent such as acetone, methyl isobutyl ketone or the like) or a sertraline organic acid salt is suspended in a solvent, and hydrochloric acid or hydrogen chloride is introduced into the solution or suspension preferably at a room temperature or the reflux temperature of the solvent to give sertraline hydrochloride crystal of metastable form. The amount of the hydrochloric acid or hydrogen chloride used is preferably 1.0–5.0 mol based on 1.0 mol of the sertraline free base or the organic salt."

U.S. Pat. No. 4,536,518, incorporated herein by reference, describes a synthesis of sertraline hydrochloride. U.S. Pat. No. 5,248,699, incorporated herein by reference, describes five crystalline forms of sertraline hydrochloride, designated Form I, Form II, Form III, Form IV and Form V. These and additional forms of sertraline hydrochloride are also disclosed in U.S. Pat. Nos. 6,452,054, 6,495,721 and 6,500,987, incorporated herein by reference.

U.S. Pat. No. 4,536,518 ("the '518 patent") describes the preparation of sertraline hydrochloride with a melting point of 243–245° C. by treating an ethyl acetate/ether solution of the free base with gaseous hydrogen chloride. The solid state properties of the sertraline hydrochloride so produced are not otherwise disclosed.

According to U.S. Pat. No. 5,248,699 ("the '699 patent"), the sertraline hydrochloride produced by the method of the '518 patent has a crystalline form denominated "Form II". The method described in the '699 patent for making Forms II and IV is by the rapid crystallization of sertraline hydrochloride from an organic solvent. An actual example is not provided.

The '699 patent discloses that Forms II, III, IV and V are metastable, and that granulation of Forms II, III or IV in isopropyl alcohol, ethyl acetate, hexane at a temperature of 40° to 60° C. causes conversion to Form I.

The preparation of sertraline hydrochloride Form II is also disclosed in WO 01/32601. In Examples 9–12, sertraline hydrochloride Form II is prepared from a maximum of 50 grams of sertraline free base in solution. The specification further discloses regarding Form II: "Sertraline hydrochloride polymorphic form II may be formed from a solution of sertraline free amine with some seeding crystals of form II before the addition of a solution of hydrogen chloride; or from a stirred suspension of sertraline hydrochloride polymorphic form V with some seeding crystals of sertraline hydrochloride polymorphic form II; or by drying a sertraline hydrochloride alcohol solvate at temperatures from about 0 to 30° C. in high vacuum (<1 mbar); or from stirred suspensions of sertraline hydrochloride polymorphic form CSC1, CSC2 or T1 with some seeding crystals of sertraline hydrochloride polymorphic form II. Furthermore, Sertraline hydrochloride polymorphic form II may be formed according to a process, wherein a solution of sertraline free amine is seeded with some crystals of polymorphic form II and a solution of hydrogen chloride is added."

WO 02/096859, also discloses processes for preparation of sertraline hydrochloride Form II. In the examples, sertraline hydrochloride is prepared from a maximum of 40 grams of sertraline mandelate salt; after obtaining a solution of the free base in isopropanol, hydrogen chloride in ethyl acetate is added at a controlled rate to obtain the hydrochloride salt.

There is a need in the art for preparation of sertraline hydrochloride Form II substantially free of other polymorphic forms of sertraline hydrochloride, particularly on an industrial scale.

SUMMARY OF THE INVENTION

In one aspect, the present invention provides a reproducible process for preparation of sertraline hydrochloride Form II substantially free of crystalline sertraline hydrochloride Form I comprising the steps of providing a solution of sertraline base, or a solution or slurry of sertraline mandelate, in an organic solvent, contacting the solution or the slurry with a flow of gaseous hydrogen chloride at a suitable rate at a temperature within the range of from about 30° C. to about 60° C., during which time sertraline hydrochloride Form II forms, wherein the temperature is kept substantially constant during the gas flow, and filtering the sertraline hydrochloride Form II at a temperature of from about 30° C. to about 60° C. to obtain sertraline hydrochloride Form II substantially free of sertraline hydrochloride Form I.

In another aspect, the present invention provides a reproducible process for preparation of sertraline hydrochloride Form II substantially free of sertraline hydrochloride Form I on an industrial scale comprising the steps of contacting a solution of sertraline base or a solution or slurry of sertraline mandelate in an organic solvent at a temperature within the range of about 30° C. to about 60° C. with a flow of gaseous hydrogen chloride to form sertraline hydrochloride Form II, and filtering the sertraline hydrochloride at a suitable temperature to obtain sertraline hydrochloride Form II containing less than about 1% sertraline hydrochloride Form I (wt/wt sertraline hydrochloride), wherein the temperature is kept substantially constant during the gas flow.

In another aspect, the present invention provides for a reproducible process for preparing sertraline hydrochloride Form II substantially free of sertraline hydrochloride Form I on an industrial scale comprising contacting a solution of sertraline base in a $C_3$ to a $C_4$ alcohol at a temperature within the range of from about 30° C. to about 60° C. with a flow of gaseous hydrogen chloride for about ½ hour to about 2 hours to obtain a slurry of sertraline hydrochloride, and filtering the slurry to obtain a sertraline hydrochloride Form II with less than about 1% sertraline hydrochloride Form I (wt/wt sertraline hydrochloride Form I/sertraline hydrochloride), wherein the temperature is kept substantially constant during the gas flow and the filtering steps.

In another aspect, the present invention provides for an industrial scale sized batch of crystalline sertraline hydrochloride Form II for preparation of a pharmaceutical oral dosage form of sertraline hydrochloride on an industrial scale, wherein the batch does not substantially convert to sertraline hydrochloride Form I when exposed to a temperature of about 40° C. and a relative humidity of about 75% for at least about 2 months. Preferably the conversion is less than about 1% weight of sertraline hydrochloride Form I to sertraline hydrochloride, more preferably the conversion is less than about 0.5% weight of sertraline hydrochloride Form I to sertraline hydrochloride, and most preferably the conversion is less than about 0.1% weight of sertraline hydrochloride Form I to sertraline hydrochloride. Preferably, the batch size is at least about 1 Kg, more preferably at least about 10 Kg. (measured after drying for a few hours at elevated temperature, such as that carried out in Example 5).

In another aspect, the present invention provides for an oral pharmaceutical dosage form prepared from an industrial scale sized batch of crystalline sertraline hydrochloride Form II, wherein the sertraline hydrochloride Form II in the oral pharmaceutical dosage form does not substantially convert over time to Form I when exposed to a temperature of about 40° C. and a relative humidity of about 75%. Preferably, the conversion is less than about 5% weight of sertraline hydrochloride Form I to sertraline hydrochloride after at least about 6 months of storage, more preferably the conversion is less than about 1% weight of sertraline hydrochloride Form I to sertraline hydrochloride after at least about 3 months of storage, and most preferably the conversion is less than about 1% weight of sertraline hydrochloride Form I to sertraline hydrochloride after at least about 1 month of storage.

In another aspect, the present invention provides for an industrial scale sized batch of crystalline sertraline hydrochloride Form II for preparation of a pharmaceutical oral dosage form of sertraline hydrochloride, wherein the batch is substantially free of sertraline hydrochloride Form I as an impurity. Preferably, the impurity is less than about 1% weight sertraline hydrochloride Form I as a wt/wt percentage to sertraline hydrochloride, more preferably the impurity is less than about 0.5%, and most preferably the impurity is less than about 0.1%.

In another aspect, the present invention provides for a tablet comprised of sertraline hydrochloride and the following excipients, in weight to weight percentages, wherein the tablet is prepared from an industrial sized batch of sertraline hydrochloride Form II substantially free of sertraline hydrochloride Form I: about 20% to about 35% sertraline hydrochloride Form II, about 25% to about 40% lactose monohydrate, about 5% to about 12% croscarmellose sodium NF, about 1% to about 3% povidone, about 20% to about 40% microcrystalline cellulose and about 0.5% to about 2.5% magnesium stearate; and methods of administration to inhibit serotonin re-uptake.

In another aspect, the present invention provides for an industrial scale sized batch of sertraline hydrochloride Form II prepared by a reproducible process on an industrial scale free of XRPD peaks at 14.1, 15.0, 15.3, 15.7, 21.2 and 26.3±0.2 degrees two theta.

In another aspect, the present invention provides an industrial sized batch of crystalline sertraline hydrochloride characterized by an X-ray powder diffraction 7232 pattern with peaks at 5.4, 10.8, 14.6, 16.3, 18.1, 19.0, 20.3, 21.8, 24.4 and 27.3±0.2 degrees two theta, with the said pattern being free of peaks between the region 15.0 to 16.0 degrees two theta, i.e., having substantially the 15.0 to 16.0 degrees two theta region depicted in FIG. 1. Preferably, the pattern is free of peaks at 15.0, 15.3 and 15.7±0.2 degrees two theta, more preferably also free of peaks at 21.2 and 26.3±0.2 degrees two theta, and most preferably also free of a peak at 14.1±0.2 degrees two theta.

DETAILED DESCRIPTION OF THE INVENTION

Percentages of sertraline hydrochloride Form I and Form II are in respect to all forms of sertraline hydrochloride combined.

The present invention provides a pure and/or stable crystalline sertraline hydrochloride Form II in a batch and pharmaceutical formulations prepared from such batch, and reproducible processes for such batch, preferably on an industrial scale. The term "batch", which is used to refer to a pharmaceutical bulk preparation, preferably on an industrial scale, such as that illustrated in Example 5, means "A specific quantity of a drug of uniform specified quality produced according to a single manufacturing order during the same cycle of manufacture." (Ansel, H et al., Pharmaceutical Dosage Forms and Drug Delivery Systems, $7^{th}$ Ed., Page 144). The term "pure" means sertraline hydrochloride Form II substantially free of sertraline hydrochloride Form I. The term "reproducible process" means a process that produces a product of a specified quality on a consistent basis.

The batch size for industrial scale is preferably at least about 0.5 Kg, more preferably at least about 1 Kg (10 liter batch volume), and most preferably at least about 10 Kg (100 liter batch volume). Example 5 illustrates such an industrial process, which prepares sertraline hydrochloride in a batch having about 20 Kg of sertraline hydrochloride.

Figure 1:
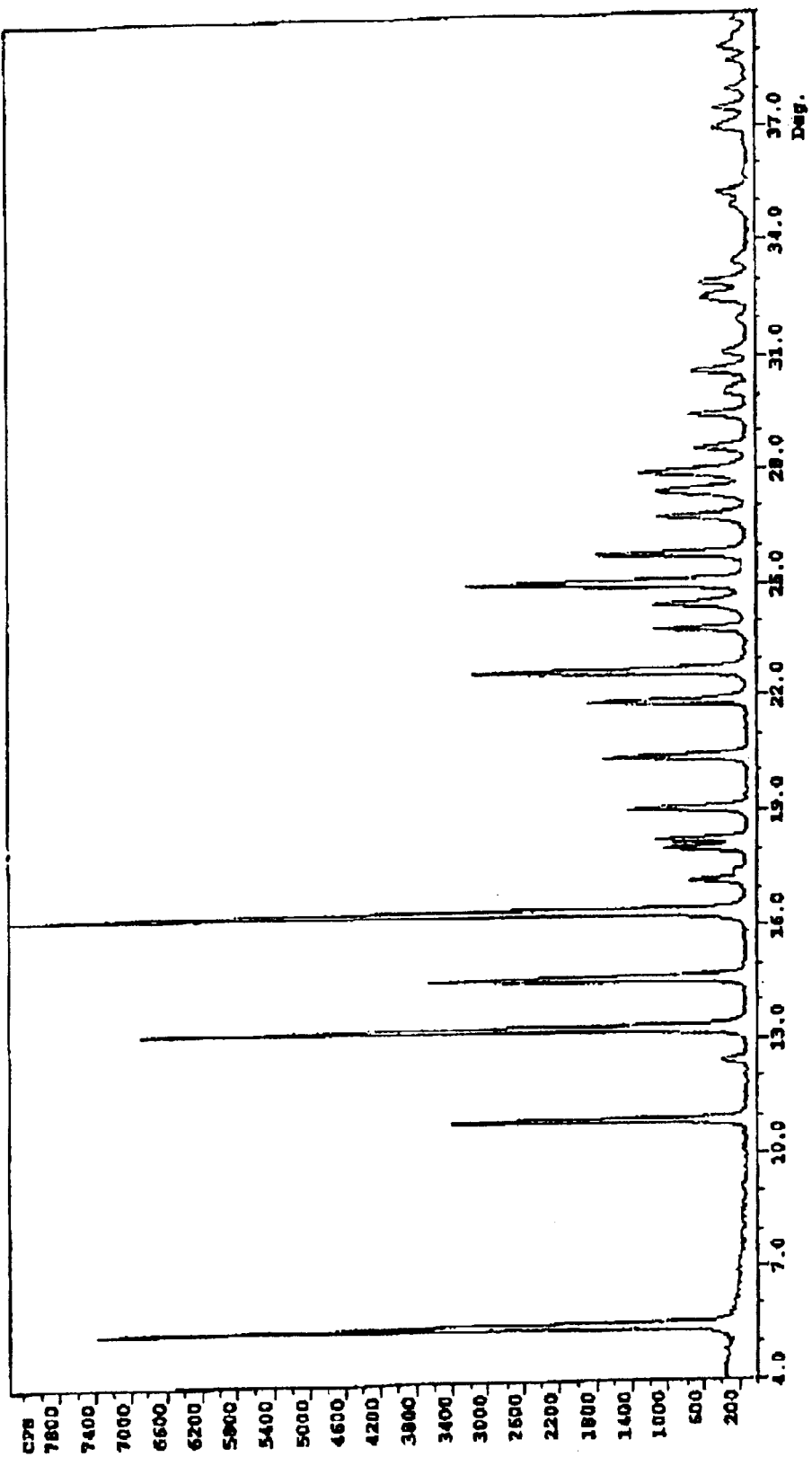
FIG. 1 is an x-ray powder diffraction pattern of sertraline hydrochloride Form II substantially free of sertraline hydrochloride Form I.

The batch of crystalline sertraline hydrochloride Form II prepared is substantially free of other crystalline forms of sertraline hydrochloride, particularly crystalline Form I of sertraline hydrochloride. The batch of the pure sertraline hydrochloride Form II preferably has a level of Form I of less than about 1%, more preferably less than about 0.5% and most preferably less than about 0.1% w/w (% of sertraline hydrochloride Form I/sertraline hydrochloride). FIG. 1 is an X-Ray powder diffraction ("XRPD") pattern which substantially depicts such pure sample of sertraline hydrochloride Form II.

Figure 2:
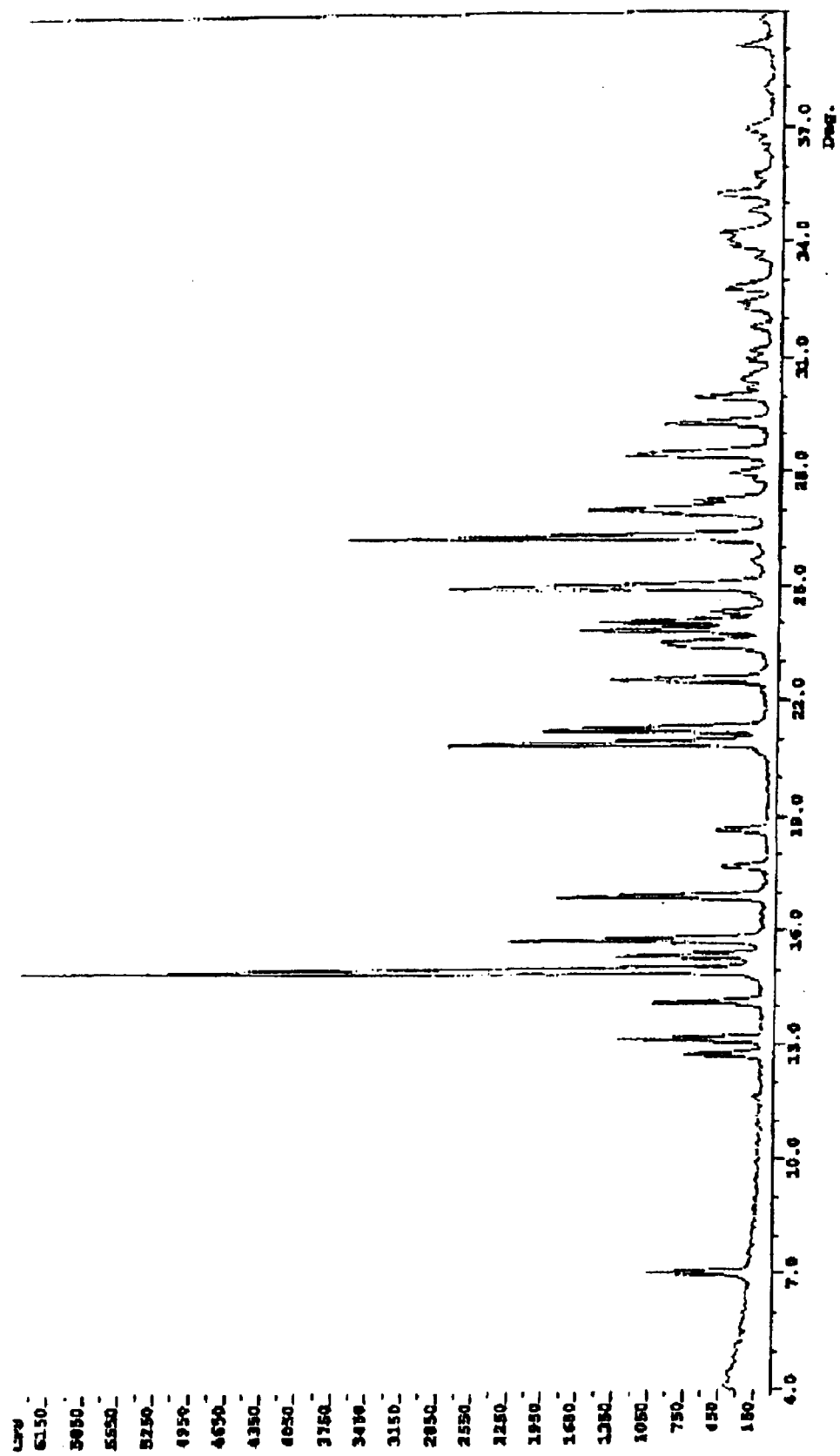
FIG. 2 is an x-ray powder diffraction pattern of sertraline hydrochloride Form I.
Figure 3:
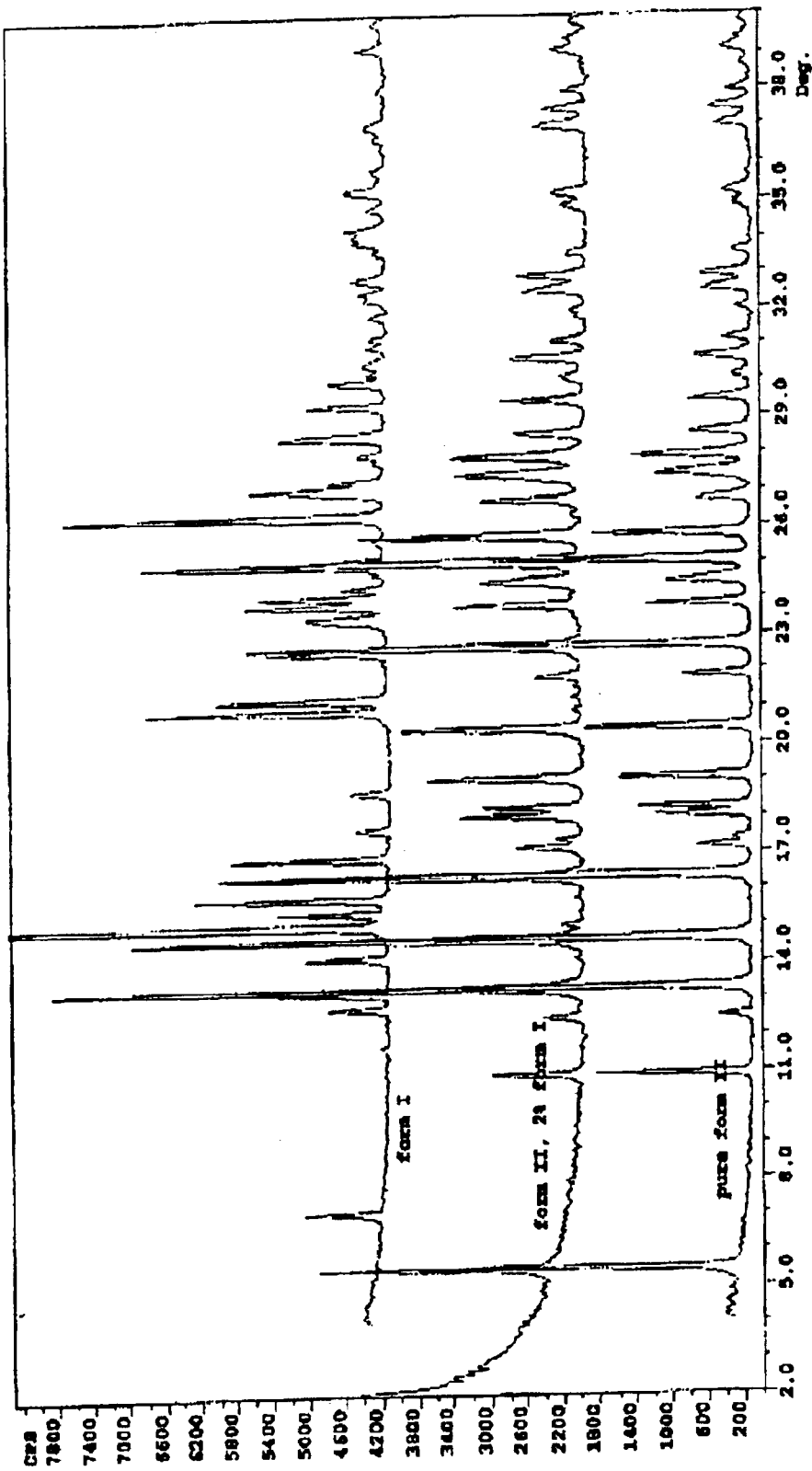
FIG. 3 is an x-ray powder diffraction pattern comparing the pattern of sertraline hydrochloride Form I, Form II and Form II containing about 2% Form I.

A suitable method for determining the presence of crystal Form I of sertraline hydrochloride in sertraline hydrochloride crystal Form II is analysis of an XRPD pattern. The XRPD pattern of sertraline hydrochloride From I (FIG. 2) is characterized by peaks at 7.1, 12.7, 14.1, 15.0, 15.3, 15.7, 20.9, 21.2, 23.5 and 26.3±0.2 degrees two theta. The XRPD of pure sertraline hydrochloride Form II (FIG. 1) is characterized by peaks at 5.4, 10.8, 14.6, 16.3, 18.1, 19.0, 20.3, 21.8, 24.4 and 27.3±0.2 degrees two theta.

Determination of presence of sertraline hydrochloride Form I in sertraline hydrochloride Form II may be made by analysis for the presence of various peaks associated with Form I, particularly at 14.1, 20.9, 21.2 and 26.3±0.2 degrees two theta and the region 15–16 degrees two theta. Preferred peaks for detection include 15.0, 15.3, 15.7, 21.2 and 26.3±0.2 degrees two theta. Under routine analytical conditions the level of detection of sertraline hydrochloride Form I in sertraline hydrochloride Form II is about 0.1% wt/wt.

The industrial sized batch of sertraline hydrochloride Form II of the present invention preferably does not substantially convert over time to Form I, preferably before formulation, upon storage at about 40° C. and about 75% relative humidity. The conversion does not occur for at least about 1–2 weeks, more preferably for at least about 1–2 months, and most preferably for at least about 3–4 months, into sertraline hydrochloride Form I. The conversion is preferably less than 1%, more preferably less than about 0.5% and most preferably less than about 0.1% w/w (% of sertraline hydrochloride Form I/sertraline hydrochloride).

The present invention also provides industrial scale processes (as well as on the lab scale) for crystallizing a highly pure and/or stable sertraline hydrochloride Form II. By controlling the process and engineering parameters, sertraline hydrochloride may be crystallized in pure Form II on a consistent basis, even on an industrial scale.

Sertraline hydrochloride Form II of the present invention is produced by contacting sertraline base in a suitable solvent with hydrogen chloride gas at a temperature range of about 30° C. to about 60° C., more preferably at a temperature of from about 30° C. to about 50° C., even more preferably of about 30° C. to about 45° C., and most preferably of about 40° C. to about 45° C. Salts, such as sertraline mandelate may also be used as a starting material. A solution or a slurry may be used with the process of the present invention, though the base is highly soluble in solvents such as n-butanol, making use of a solution preferable with the base.

Suitable solvents are those that allow for crystallization of sertraline hydrochloride Form II substantially free of sertraline hydrochloride Form I. Examples of such solvents for preparation of Form II are disclosed in U.S. Pat. Nos. 6,495,721 and 6,500,987, incorporated herein by reference. Examples of such solvents include cyclohexane, isopropanol, n-propanol, 2-butanol, t-butanol, i-butanol, n-butanol (also known as 1-butanol), ethyl acetate, acetone, hexane, t-butyl-methyl ether, DMF, and mixtures thereof, particularly mixtures of n-butanol and DMF. From the above $C_3$ to $C_4$ alcohols, a preferred alcohol is n-butanol.

A process criteria for crystallization of sertraline hydrochloride pure Form II is the stability of the temperature during crystal formation of pure Form II. Once a desired temperature is achieved, the temperature is substantially maintained, i.e. within about ±5° C. in the specified range (See e.g. Example 5). The ±5° C. allowance does not take the process out of the recited temperature range (See e.g. Example 5).

The process is carried out by adding hydrogen chloride gas to the solution. Preferably, the gas flow is relatively fast, but a gas flow that is too fast may cause operational problems. One problem is rapid precipitation, which may cause difficulty in stirring. Chemical purity or polymorphic purity may also be adversely affected by a very fast gas flow.

The optimal amount of gas flow is dependent on the scale of the process. Preferably, the gas flow is of about 4 to about 6 grams of gaseous hydrogen chloride per hour per about 25 grams of sertraline base. Based on this guidance, one of skill in the art would appreciate the proper amount of gas flow when sertraline mandelate or another salt is used as a starting material.

In a laboratory scale (about 1 liter reactor) or production (industrial) scale (about 100 to about 630 liter reactors (i.e. a batch volume in this size range is prepared; The batch volume for industrial scale may be smaller, for example at least about 5/10 liters, which would give product of about at least about 0.5/1 Kg respectively), the duration of the gas flow is preferably less than about 2 hours, more preferably about 1 hour. When the gas flow lasts for long durations, traces of sertraline hydrochloride Form I inconsistently appear in small amounts (2–3% weight of sertraline hydrochloride Form I to sertraline hydrochloride). The gas flow is preferably for the duration of about ½ hour to about 2 hours, more preferably of about ¾ hour to about 1¼ hour, and most preferably for about 1 hour. One of skill in the art appreciates that the optimal duration of the gas flow and the flow rate are dependent on the specifics of a bubbling process, such as the size of the bubbles.

The pH of the resulting slurry may be used to monitor the gas flow. The gas flow is preferably stopped when reaching a pH of less than about 1.0, more preferably when reaching a pH of at least about 0.5.

The substantially pure Form II may the be recovered from the slurry by techniques well known in the art. In a particularly preferred embodiment, sertraline hydrochloride Form II is recovered by filtration. The temperature during filtration is preferably maintained from-about 30° C. to about 60° C., more preferably about 30° C. to about 50° C., even more preferably from about 30° C./35° C. to about 45° C. and most preferably at a temperature of from about 40° C. to about 45° C. (about the same range as the HCl addition step). The temperature is preferably the same as that during the HCl addition, and more preferably the temperature is kept substantially constant from the beginning of the HCl addition to the end of the filtration step. (See e.g. Example 5)

Sertraline hydrochloride Form II is kinetically stable when crystallized as a highly pure sertraline hydrochloride Form II. The highly pure sertraline hydrochloride Form II is stable during storage under stress conditions for at least about 2 weeks, more preferably for at least about 1–2 months, even more preferably for at least about 3 months and most preferably for at least about 6 months. In contrast, sertraline hydrochloride Form II that contains trace amounts of sertraline hydrochloride Form I (at least about 1% w/w of sertraline hydrochloride Form I/sertraline hydrochloride) is not stable during storage under such stress condition.

Without being bound by theory, it is believed that the level of purity presently achieved in the highly pure sertraline hydrochloride Form II imparts the polymorph with stability. It is believed that an unstable composition of sertraline hydrochloride Form II contains trace amounts of sertraline hydrochloride Form I, the presence of which facilitates the conversion of sertraline hydrochloride Form II to sertraline hydrochloride Form I, perhaps by providing a seed for crystallization.

The present invention also provides a pharmaceutical formulation, particularly oral dosage forms such as tablets containing fine crystals of highly pure sertraline hydrochloride Form II. The active ingredient of the formulation, sertraline hydrochloride Form II, does not substantially convert into sertraline hydrochloride Form I. Hence it is possible to formulate unit dosages such as tablets that are stable during storage.

Storage of a tablet containing highly pure sertraline hydrochloride Form II at about 40° C. and about 75% relative humidity, for at least about 1–2 weeks, more preferably from about 1–2 months and most preferably for at least about 3–4 months does not show any significant conversion to other polymorphic forms of sertraline hydrochloride, especially the stable Form I. Preferably, less than about 5%, more preferably, less than about 3% and most preferably, less than about 1% of the sertraline hydrochloride Form II in a tablet converts to polymorphic Form I of sertraline hydrochloride following storage of the tablet.

The detection of sertraline hydrochloride Form I in a pharmaceutical formulation, to the extent of about 1% w/w (% of sertraline hydrochloride Form I/sertraline hydrochloride), may be accomplished by use of x-ray powder diffraction.

As in bulk sertraline hydrochloride Form II, the X-ray powder diffraction pattern of pure sertraline hydrochloride tablet does not show a substantial polymorphic change to Form I.

Pharmaceutical compositions of the present invention contain highly pure sertraline hydrochloride Form II. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®, colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants may be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which may cause the product to have pitting and other surface irregularities. A lubricant may be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, sertraline hydrochloride and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Preferably, the pharmaceutical formulations of the present invention are solid dosage forms in the form of a tablet for the oral administration of sertraline hydrochloride. The highly pure sertraline hydrochloride Form II used for preparing a tablet may be in the form of fine crystals. Preferably, the fine crystals have a particle size distribution such that 100% of the particles are below 200 microns, more preferably below 100 microns and most preferably below about 50 microns.

Methods known in the art, as described above, may be used to prepare tablets of sertraline hydrochloride Form II. Highly pure sertraline hydrochloride Form II tablets may be prepared for instance by mixing the active ingredient, sertraline hydrochloride pure Form II, with a combination of excipients including, lactose, povidone, microcrystalline cellulose and croscarmellose sodium. Purified water may be added to the powder mixture of sertraline modification II and excipients. The mixture may be then dried until only trace amounts of fluid remain in the granulate as residual moisture. Preferably, the mixture is dried to a loss on drying ("LOD") no more than ("NMT") about 0.5 to about 3%. The granulate may be then sieved, and magnesium stearate may be added to the milled granulate. The final blend of sertraline modification II, excipients and magnesium stearate is compressed into tablets and may be film coated, preferably with Opadry® (Colorcon, Westpoint Pa.). According to Colorcon, Opadry® is a one-step customized coating system that combines polymer, plasticizer, and if desired, a pigment in dry concentrate. Table 1 shows suitable ranges of active ingredients and excipients (weight %) and the preferred amounts for the present pharmaceutical formulations.

TABLE 1

| Material | Range of % composition (w/w) | Preferred % composition | Function |
|---|---|---|---|
| High purity sertraline modification II | 20–35% | 28.0 | Active ingredient |
| Lactose Monohydrate | 25–40 | 32.0 | Filler |
| Croscarmellose Sodium NF | 5–12 | 10.0 | Disintegrant |
| Povidone USP (PVP K-30) | 1–3 | 2.4 | Binder |
| Microcrystalline Cellulose NF (Avicel PH 102) | 20–40 | 26.6 | Filler and disintegrant |
| Purified water USP | — | — | Granulation processing solvent |
| Magnesium Stearate NF | 0.5–2.5 | 1.0 | Lubricant |

*Granulation processing solvent only (dried to achieve moisture content of LOD-NMT about 0.5–1.5%).

In accordance with the present invention, the pharmaceutical formulations of the present invention are useful for inhibiting the re-uptake of serotonin, thus resulting in an increased level of serotonin. An increased level of serotonin alleviates symptoms of psychiatric disorders such as depression. The oral pharmaceutical dosage forms of the present invention preferably contain of about 20 mg to about 100 mg of the base equivalent of sertraline hydrochloride, with about 25 mg, about 50 mg and about 100 mg tablets being preferred.

Instrumentation Used:

X-Ray powder diffraction data was obtained by using a SCINTAG powder X-Ray diffractometer model X'TRA equipped with a solid state detector. Copper radiation of 1.5418 Å was used. The diffractometer was equipped with a round aluminum sample holder with round zero background quartz plate having a cavity of 25(diameter)*0.5(depth) mm.

EXAMPLES

Example 1

Stability of bulk sertraline hydrochloride Form II and tablet

| Polymorph Content of sertraline hydrochloride in tablet | Polymorph Content of bulk sertraline hydrochloride | Length of Storage |
|---|---|---|
| 40° C., 75% RH Polymorphic Form detected (I or II) | 40° C., 75% RH Polymorphic Form detected (I or II) | |
| II > I (<1%) | II > I (<1%) | t = 0 |
| II > I (<3%) | II > I (<1%) | 1 month |
| II > I (<3%) | II > I (2%) | 2 months |
| II > I (3%) | II > I (2%) | 3 months |
| — | II > I (4%) | 4 months |

Example 2

Stability of highly pure bulk sertraline hydrochloride Form II and tablet

| Polymorph Content of sertraline hydrochloride in tablet | Polymorph Content of bulk sertraline hydrochloride | Length of Storage |
|---|---|---|
| 40° C., 75% RH Polymorphic Form detected (I or II) | 40° C., 75% RH Polymorphic Form detected (I or II) | |
| II* | II* | t = 0 |
| II | II | 1 month |
| II | II | 2 months |
| — | — | 3 months |
| — | II | 6 months |

*The presence of Form I was below the detection level in Examples 2–4. The detection level for the tablet was less than about 1% weight of sertraline hydrochloride Form I to the weight of sertraline hydrochloride, and in the bulk less than about 0.1%.

Example 3

Stability of highly pure bulk sertraline hydrochloride Form II and tablet

| Polymorph Content of sertraline hydrochloride in tablet | Polymorph Content of bulk sertraline hydrochloride | Length of Storage |
|---|---|---|
| 40° C., 75% RH Polymorphic Form detected (I or II) | 40° C., 75% RH Polymorphic Form detected (I or II) | |
| II | II | t = 0 |
| II | II | 1 month |
| II | II | 2 months |
| — | — | 3 months |
| — | II | 6 months |

Example 4

Stability of highly pure bulk sertraline hydrochloride Form II and tablet

| Polymorph Content of sertraline hydrochloride in tablet | Polymorph Content of bulk sertraline hydrochloride | Length of Storage |
|---|---|---|
| 40° C., 75% RH Polymorphic Form detected (I or II) | 40° C., 75% RH Polymorphic Form detected (I or II) | |
| II | II | t = 0 |
| II | II | 1 month |
| II | II | 2 months |
| — | — | 3 months |
| — | II | 6 months |

Example 5
Preparation of Pure Sertraline Hydrochloride Form II in Lot (Industrial) Scale Sertraline base (27 kg) obtained directly from synthesis was dissolved in 105 kg of n-butanol. The solution was treated for 1 hour with 1 kg carbon at 40° C.–45° C., filtered and washed with 25 kg n-butanol. The solution was reheated to 40° C.–45° C. and the achieved temperature was kept constant during the gas flow and filtration. Hydrogen chloride gas was added at the rate of 4.5–5 kg/hr for the duration of 1 hour until pH 0.5 or less was reached. Immediately after, the slurry was filtered at 40° C.–45° C. The cake was washed with 25 kg of n-butanol, and dried for about 4 hours at 80° C. The yield was 70% (21.2 Kg).

Example 6
Preparation of Pure Sertraline Hydrochloride Form II in Lab Scale

Sertraline base (26 g) obtained directly from the synthesis was dissolved in n-butanol (6 volumes) (140 ml). The solution was treated for 1 hour with 1.1 g carbon at 40° C.–45° C., filtered and washed with 12 cc n-butanol. The solution was reheated to 40° C.–45° C. and the temperature achieved was kept constant during the gas flow and filtration. Hydrogen chloride gas was added at the rate of 4–6 g/hr for the duration of 1 hour until pH 0.5 or less was reached. Immediately after, the slurry was filtered at 40° C.–45° C. The cake was washed with 30 ml of n-butanol, and dried for about 4 hours at 80° C.

Example 7
Preparation of Sertraline Hydrochloride in n-BuOH at 70° C.

Sertraline base (30 g) in n-BuOH (240 ml) was heated to 50° C. HCl(g) was bubbled to the solution and the temperature rose to 70° C.; when the pH reached 1.5, precipitation was observed (the temperature was 68° C. More HCl was purged through the slurry (the temperature was 65° C.). After the pH reached 0.5, the mixture was cooled to room temperature and a solid was filtrered and washed with n-BuOH. After drying, a mixture of sertraline hydrochloride form II and form I was obtained (26.41 g).

Example 8
Preparation of Sertraline Hydrochloride in n-BuOH by Filtration at 10° C.

Sertraline base (30 g) was dissolved in n-BuOH(240 ml) and HCl (g) was bubbled through the solution. The temperature rose to 45° C. The reaction mixture turned to a gelly like mixture, which then became a slurry. The slurry was cooled to 10° C. and a solid was filtered, and washed with n-BuOH. After drying, a mixture of sertraline hydrochloride form II and I was obtained (25.9 g).

Example 9
Preparation of Sertraline Hydrochloride Form II in n-BuOH from Sertraline Mandelate Sertraline mandelate (20 g) in n-BuOH (400 ml) was heated to 60° C. A slurry was obtained. HCl (g) was bubbled through the mixture and complete dissolution was observed. When the solution pH was ~0.5, the solution was cooled and seeded with sertraline hydrochloride Form II. The reaction mixture was srirred at room temperature over night and a solid was filtered and washed with n-BuOH. The solid was dried to afford sertraline hydrochloride Form II (7.21 g).

Having thus described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 may be used as a guidance. All references and priority documents mentioned herein are incorporated by reference in their entirety.

What is claimed is:

1. A reproducible process for preparation of sertraline hydrochloride Form II comprising the steps of:
   a) providing a solution of sertraline base, or a solution or slurry of sertraline mandelate, in an organic solvent;
   b) contacting the solution or the slurry with a flow of gaseous hydrogen chloride at a temperature within the range of from about 30° C. to about 60° C., during which time sertraline hydrochloride Form II forms, wherein the temperature is kept substantially constant during the gas flow; and
   c) filtering the sertraline hydrochloride Form II at a temperature of from about 30° C. to about 60° C. to obtain sertraline hydrochloride Form II containing less than about 1% sertraline hydrochloride Form I as measured wt/wt sertraline hydrochloride Form I/sertraline hydrochloride.

2. The process of claim 1, wherein the solvent is an alcohol.

3. The process of claim 2, wherein the alcohol is a $C_3$ or a $C_4$ alcohol, or mixtures thereof.

4. The process of claim 3, wherein the alcohol is n-butanol.

5. The process of claim 1, wherein the solvent is selected from the group consisting of cyclohexane, ethyl acetate, acetone, hexane, t-butyl-methyl ether, DMF, and mixtures thereof.

6. The process of claim 1, wherein the solution of sertraline base is provided.

7. The process of claim 6, wherein the gas flows at a rate of about 4 to about 6 grams of gaseous hydrogen chloride per hour per about 25 grams of sertraline base.

8. The process of claim 1, wherein the temperature during the gas flow is about 30° C. to about 50° C.

9. The process of claim 8, wherein the temperature is about 35° C. to about 50° C.

10. The process of claim 9, wherein the temperature is about 40° C. to about 45° C.

11. The process of claim 1, wherein the gas flow is stopped when reaching a pH of less than about 1.

12. The process of claim 1, wherein the temperature is kept substantially constant during the gas flow and the filtering steps.

13. The process of claim 1, wherein the gas flow is stopped in less than about 2 hours.

14. The process of claim 1, wherein the amount of sertraline hydrochloride Form is less than about 0.5%.

15. The process of claim 14, wherein the amount of sertraline hydrochloride Form I is less than about 0.1%.

16. The process of claim 1, wherein the process results in at least about 0.5 kg of sertraline hydrochloride Form II after the filtering step.

17. The process of claim 16, wherein at least about 1 Kg of sertraline hydrochloride Form II is obtained after the filtering step.

18. The process of claim 17, wherein at least about 10 Kg of sertraline hydrochloride Form II is obtained after the filtering step.

19. The process of claim 16, wherein at least about a 100 liter solution is provided.

20. A reproducible process for preparation of sertraline hydrochloride Form II comprising the steps of contacting a solution of sertraline base, or a solution or slurry of sertraline mandelate in an organic solvent, at a temperature within the range of about 30° C. to about 60° C. with a flow of gaseous hydrogen chloride to form sertraline hydrochloride Form II, and filtering the sertraline hydrochloride to obtain sertraline hydrochloride Form II containing less than about 1% sertraline hydrochloride Form I (wt/wt sertraline hydrochloride), wherein the temperature is kept substantially constant during the gas flow.

21. The process of claim 20, wherein the solution of sertraline base is used.

22. The process of claim 21, wherein the gas flows at a rate of about 4 to about 6 grams of gaseous hydrogen chloride per hour per about 25 grams of sertraline base.

23. The process of claim 20, wherein the solvent is an alcohol.

24. The process of claim 23, wherein the alcohol is a $C_3$ or a $C_4$ alcohol, or mixtures thereof.

25. The process of claim 24, wherein the alcohol is n-butanol.

26. The process of claim 20, wherein the solvent is selected from the group consisting of cyclohexane, ethyl acetate, acetone, hexane, t-butyl-methyl ether, DMF, and mixtures thereof.

27. The process of claim 20, wherein the temperature is about 30° C. to about 50° C. during the gas flow.

28. The process of claim 27, wherein the temperature is about 30° C. to about 45° C.

29. The process of claim 28, wherein the temperature is about 40° C. to about 45° C.

30. The process of claim 20, wherein the filtering is carried out at a temperature of from about 30° C. to about 60° C.

31. The process of claim 20, wherein the temperature is kept substantially constant during the gas flow and the filtering step.

32. The process of claim 20, wherein at least about 1 Kg of sertraline hydrochloride Form II is obtained after the filtering step.

33. The process of claim 32, wherein at least about 10 Kg of sertraline hydrochloride Form II is obtained after the filtering step.

34. The process of claim 20, wherein at least about a 100 liter solution is prepared.

35. A reproducible process for preparing sertraline hydrochloride Form II comprising contacting a solution of sertraline base in a $C_3$ to a $C_4$ alcohol at a temperature within the range of from about 30° C. to about 60° C. with a flow of gaseous hydrogen chloride for about ½ hour to about 2 hours to obtain a slurry of sertraline hydrochloride, and filtering the slurry to obtain sertraline hydrochloride Form II with less than about 1% sertraline hydrochloride Form I (wt/wt sertraline hydrochloride Form I/sertraline hydrochloride), wherein the temperature is kept substantially constant during the gas flow and the filtering steps.

36. The process of claim 35, wherein the temperature is from about 35° C. to about 50° C.

37. The process of claim 35, wherein the alcohol is n-butanol.

38. The process of claim 35, wherein at least about 1 Kg of sertraline hydrochloride Form II is obtained after the filtering step.

39. The process of claim 1, 20 or 35, wherein at temperature is about 30° C. to about 45° C.

* * * * *

UNITED STATES PATENT AND TRADEMARK OFFICE
CERTIFICATE OF CORRECTION

PATENT NO.      : 6,897,340 B2
DATED           : May 24, 2005
INVENTOR(S)     : Ronen Borochovitch et al.

It is certified that error appears in the above-identified patent and that said Letters Patent is hereby corrected as shown below:

<u>Title page,</u>
Item [57], ABSTRACT,
Line 2, change "substantilly" to -- substantially --.

<u>Column 4,</u>
Line 55, remove "7232".

<u>Column 5,</u>
Lines 39 and 40, change "preferrably" to -- preferably --.

<u>Column 6,</u>
Lines 6 and 7, change "preferrably" to -- preferably --.

<u>Column 7,</u>
Line 35, change "preferrably" to -- preferably --.

<u>Column 9,</u>
Line 47, change "guconic" to -- gluconic --.
Line 48, change "goconate" to -- gluconate --.
Line 67, change "losenges" to -- lozenges --.

<u>Column 13,</u>
Line 25, change "filtrered" to -- filtered --.
Line 33, change "gelly" to -- jelly --.
Line 47, change "srirred" to -- stirred --.

<u>Column 14,</u>
Line 43, change "Form" to -- Form I --.

UNITED STATES PATENT AND TRADEMARK OFFICE
CERTIFICATE OF CORRECTION

PATENT NO. : 6,897,340 B2
DATED : May 24, 2005
INVENTOR(S) : Ronen Borochovitch et al.

It is certified that error appears in the above-identified patent and that said Letters Patent is hereby corrected as shown below:

Column 16,
Line 26, change "wherein at temperature" to -- wherein the temperature --.

Signed and Sealed this

Third Day of January, 2006

JON W. DUDAS
*Director of the United States Patent and Trademark Office*